US007186857B2

(12) United States Patent
Müller et al.

(10) Patent No.: US 7,186,857 B2
(45) Date of Patent: Mar. 6, 2007

(54) PROCESS FOR THE PREPARATION OF DI- AND POLYAMINES OF THE DIPHENYLMETHANE SERIES

(75) Inventors: Heinz-Herbert Müller, Krefeld (DE); Stefan Wershofen, Mönchengladbach (DE); Stefan Grabowski, Dormagen (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 11/257,713

(22) Filed: Oct. 25, 2005

(65) Prior Publication Data

US 2006/0094897 A1    May 4, 2006

(30) Foreign Application Priority Data

Oct. 28, 2004    (DE) ...................... 10 2004 052 370

(51) Int. Cl.
 *C07C 211/00* (2006.01)
 *C07C 265/12* (2006.01)
 *C07C 263/00* (2006.01)
(52) U.S. Cl. ................ 560/330; 560/347; 564/326
(58) Field of Classification Search ............... 564/326
 See application file for complete search history.

(56) References Cited

U.S. PATENT DOCUMENTS

| 6,720,455 B2 | 4/2004 | Hagen et al. ............. 564/333 |
| 2003/0045745 A1 | 3/2003 | Hagen et al. ............. 560/359 |
| 2003/0176626 A1* | 9/2003 | Hagen et al. ............. 528/310 |

OTHER PUBLICATIONS

Chem. Soc. Rev., 3(2), (month unavailable) 1974, H.J. Twitchett, pp. 209-231, "Chemistry of the Production of Organic Isocyanates".
Kirk-Othmer Encycl. Chem. Technol., 3$^{rd}$, ed., 2, (month unavailable) 1978, William M. Moore, pp. 338-348, "Methylenedianiline".

* cited by examiner

*Primary Examiner*—Paul A. Zucker
(74) *Attorney, Agent, or Firm*—Joseph C. Gil; Lyndanne M. Whalen; N. Denise Brown

(57) ABSTRACT

The present invention relates to a process for the preparation of di- and polyamines of the diphenylmethane series, and to the preparation of di- and poly-isocyanates of the diphenylmethane series from these di- and poly-amines. The di- and poly-amines of the diphenylmethane series are prepared by the reaction of aniline and formaldehyde in the presence of hydrochloric acid. In with the present invention, the hydrochloric acid employed contains less than 0.001 wt. % of metal ions which are divalent and/or more than divalent.

5 Claims, No Drawings

PROCESS FOR THE PREPARATION OF DI- AND POLYAMINES OF THE DIPHENYLMETHANE SERIES

CROSS REFERENCE TO RELATED PATENT APPLICATION

The present patent application claims the right of priority under 35 U.S.C. § 119 (a)–(d) of German Patent Application No. 10 2004 052 370.3, filed Oct. 28, 2004.

BACKGROUND OF THE INVENTION

The present invention relates to a process for the preparation of di- and polyamines of the diphenylmethane series.

Di- and polyamines of the diphenylmethane series are understood as meaning compounds and compound mixtures of the following structure:

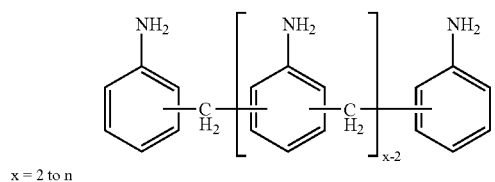

x = 2 to n wherein n represents a natural number>2.

The continuous, discontinuous, or semi-continuous preparation of di- and polyamines of the diphenylmethane series, also called MDA in the following text, is described in numerous patents and publications. See e.g. H. J. Twitchett, Chem. Soc. Rev. 3(2), 209 (1974), M. V. Moore in: Kirk-Othmer Encycl. Chem. Technol., 3rd ed., New York, 2, 338–348 (1978). The preparation of these polyamines is conventionally carried out by reaction of aniline and formaldehyde in the presence of acidic catalysts. Aqueous HCl is conventionally employed as the acidic catalyst. According to the prior art, the acidic catalyst is neutralized by addition of a base, and thus, used up at the end of the process, and before the final working up steps (such as, for example, removal of excess aniline by distillation).

The di- and polyisocyanates of the diphenylmethane series, called MDI in the following text, are prepared by phosgenation of the corresponding di- and polyamines. The di- and polyisocyanates of the diphenylmethane series which are prepared in this way thereby contain the various isocyanate isomers and higher homologues thereof in the same composition as the polyamines from which they have been prepared.

In the course of the preparation of MDA, the acidic reaction mixture is then conventionally neutralized with a base. After the neutralization, the organic phase is conventionally separated from the aqueous phase in a separating container. The product-containing organic phase which remains after the aqueous phase has been separated off is then conventionally subjected to further working up steps, such as a washing with water, and then freed from excess aniline and other substances present in the mixture (e.g. further solvents) by, for example, distillation, extraction or crystallization.

Experience in the plant shows, however, the separating off of the aqueous phase from the product-containing organic phase after the neutralization and/or the subsequent washing, may be severely impaired by the formation of a third phase (rag or rag layer). This third phase is a stable, possibly voluminous intermediate phase, which occurs between the aqueous and the organic phase, and makes phase separation difficult. In the extreme case, this third phase even prevents phase separation completely. In the most adverse case for the process in the plant, the phase separation tank or tanks affected must be emptied completely and cleaned. The content of the phase separation tank or tanks then has to be worked up or disposed of with great effort, which is associated with considerable costs. Under certain circumstances this can also lead to the continuous production having to be interrupted.

The object of the present invention was, therefore, to provide a simple and economical process for the preparation of di- and polyamines of the diphenylmethane series, in which the separating off of the aqueous phase from the product-containing organic phase, after the neutralization and/or the subsequent washing, can be carried out simply and without trouble.

SUMMARY OF THE INVENTION

The invention relates to a process for the preparation of di- and polyamines of the diphenylmethane series. This process comprises reacting aniline with formaldehyde in the presence of hydrochloric acid, wherein the hydrochloric acid employed contains less than 0.001 wt. % of metal ions which are divalent and/or more than divalent.

Another aspect of the present invention is a process for the preparation of di- and polyisocyanates of the diphenylmethane series from these di- and polyamines of the diphenylmethane series. This process comprises reacting the di- an polyamines of the diphenylmethane series that are produced by the previously described process with phosgene, to yield the corresponding di- and polyisocyanates of the diphenylmethane series.

DETAILED DESCRIPTION OF THE INVENTION

In accordance with the present invention, the limit of <0.001 wt. % relates to the sum of the concentrations of the metal ions which are divalent and/or metal ions which are more than divalent. Preferably, the hydrochloric acid employed in the present invention contains <0.0005 wt. % (i.e. 0 to <0.0005 wt. %), and most preferably <0.0003 wt. % (i.e. 0 to <0.0003 wt. %) of metal ions which are divalent and/or metal ions which are more than divalent.

The hydrochloric acid required for the preparation of MDA can originate from various sources or processes. For example, the hydrogen chloride that is liberated during the reaction of amines with phosgene can be absorbed in water or dilute hydrochloric acid. Hydrogen chloride from chlorinations of organic substrates can also be utilized in a similar manner. The use of hydrochloric acid in which the concentration of metal ions which are divalent and/or metal ions which are more than divalent has been lowered to contents of <0.001 wt. %, for example, by precipitation in the form of sparingly soluble salts, is also possible. In this context, the hydrochloric acid conventionally has a concentration of HCl of 25–36 wt. %, but higher or lower concentrations are also possible.

As used in the present application, the phrase metal ions which are divalent and/or more than divalent is understood as meaning ions in an oxidation level≧+2 of the metals originating from main groups 2 to 6, subgroups 1 to 8, the lanthanide series and/or the actinide series of the periodic table of the elements. Examples of such metals include, for example, alkaline earth metals, such as magnesium and calcium, or also metals such as aluminium and iron. The concentrations of the individual metal ions in the hydrochloric acid here are preferably <0.0003 wt. %.

The process according to the invention can be carried out both continuously, and semi-continuously, and also discontinuously.

Polyamines of the diphenylmethane series can be prepared with degrees of protonation of <15% by the process of the present invention, but higher degrees of protonation are also possible. In this context, in the case of hydrochloric acid the molar ratio of the amount of hydrochloric acid employed and the molar amount of amine functions present in the reaction mixture is called the degree of protonation.

Suitable polyamine mixtures of the diphenylmethane series are conventionally obtained by condensing aniline with formaldehyde in the molar ratio of 1.5:1 to 20:1.

Conventionally, formaldehyde is employed industrially as an aqueous solution which is present in concentrations of 30–50 wt. %. However, it is also possible to employ aqueous formaldehyde solutions of another concentration, or other compounds which supply methylene groups. Other such suitable compounds include, for example, as e.g. polyoxymethylene glycol, para-formaldehyde or trioxane.

In one embodiment of the process of the invention, the process comprises first mixing aniline with hydrochloric acid, and then adding formaldehyde to the mixture. Likewise, however, it is also possible to mix aniline, formaldehyde and hydrochloric acid in another sequence, or also to mix these simultaneously.

In accordance with the present invention, the process can be carried out, e.g,. by a procedure comprising introducing aniline, formaldehyde solution and hydrochloric acid into a stirred tank, and mixing, and optionally, in parallel with the reaction which occurs, removing or separating some of the water by distillation. In a discontinuous process, aniline, formaldehyde solution and hydrochloric acid can optionally be added over time-based metering profiles, with it being possible to separate off the water during or after the addition of the educts by, for example, means of vacuum distillation. Preferably, the mixing of aniline, formaldehyde solution and aqueous HCl takes place at temperatures of 20 to 60° C.

In another embodiment, the invention comprises first mixing aniline and formaldehyde and reacting in the absence of the acidic catalyst at temperatures of 20° C. to 100° C., preferably 40° C. to 100° C., and most preferably 60° C. to 95° C. Condensation products of aniline and formaldehyde (i.e. so-called aminal) form during this procedure. After the aminal formation, the water contained in the aminal is at least partly removed by, for example, phase separation or by other suitable processes such as, for example, by distillation.

The addition of the acidic catalyst and the removal of the water can be carried out by, for example, a procedure in which aqueous HCl is introduced into a stirred tank containing the aminal produced, and optionally some of the water is removed by separating off by distillation during the reaction to give the condensation product.

In a preferred variation of this embodiment of the present invention, the process first comprises mixing aniline and formaldehyde are reacting in the absence of the acidic catalyst, at temperatures of 20° C. to 100° C., preferably 40° C. to 100° C., and most preferably 60° C. to 95° C. Condensation products of aniline and formaldehyde (so-called aminal) form during this procedure. After the aminal formation, the water contained in the aminal is at least partly removed, for example, by phase separation or by other suitable processes such as, for example, by distillation.

Then, the aminal is mixed with hydrochloric acid, preferably at temperatures of 20 to 60° C. and preferably with specific power inputs of greater than 10 kW/m$^3$.

The further reaction of the reaction mixture which is obtained according to one of the above embodiments is carried out in conventional reaction apparatuses. For example, suitable apparatuses include stirred reactors, tube reactors and/or tube reactors with baffles such as perforated trays, which influence the residence time characteristics in the reactor. A combination of several types of reactor is also suitable.

Preferably, the temperature of the reaction mixture is brought in stages, or is continuously, and optionally, under increased pressure to a temperature of 110° C. to 250° C., more preferably of 110° C. to 180° C., and most preferably of 110° C. to 160° C. The residence time required is chosen such that complete conversion is ensured.

The reaction of aniline and formaldehyde in the presence of hydrochloric acid can also be carried out in the presence of further substances. Other suitable substances include, for example, salts, organic acids, or inorganic acids.

In order to work up the acidic reaction mixture, the reaction mixture is conventionally neutralized with a base. According to the prior art, the neutralization is conventionally carried out at temperatures of, for example, 90 to 100° C., without the addition of further substances. (See H. J. Twitchett, Chem. Soc. Rev. 3(2), 223 (1974)). However, neutralization can also be carried out at another temperature level, in order to accelerate the breakdown of troublesome by-products. Suitable bases include, for example, the hydroxides of the alkali and alkaline earth metals. Aqueous NaOH is preferably used.

It is preferred that the base employed for the neutralization is employed in amounts of greater than 100%, and more preferably in 105% to 120% of the amount required stoichiometrically for the neutralization of the acidic catalyst employed.

After the neutralization, the organic phase is conventionally separated from the aqueous phase in a separating tank. The product-containing organic phase which remains after the aqueous phase has been separated off, is then conventionally subjected to additional working up steps (e.g. washing with water), and is then freed from excess aniline and other substances present in the mixture (e.g. further solvents) by suitable processes such as, for example, distillation, extraction or crystallization.

In accordance with the present invention, by the use of hydrochloric acid which contains less than 0.001 wt. % of metal ions which are divalent and/or more than divalent, the separating off of the aqueous phase from the MDA-containing organic phase after the neutralization and/or the subsequent washing, can be carried out simply and without trouble. This is due to the low contents of metal ions which are divalent and/or more than divalent in the hydrochloric acid which have the effect that a third phase (i.e. rag or a rag layer) which interferes with the phase separation or makes phase separation difficult, is no longer formed.

The di- and polyamines prepared in this way can be reacted with phosgene in an inert organic solvent by the known methods to yield the corresponding di- and polyisocyanates of the diphenylmethane series, MDI. The molar ratio of crude MDA to phosgene is expediently chosen such that 1 to 10 mol, and preferably 1.3 to 4 mol, of phosgene are present in the reaction mixture per mol of $NH_2$ group. Chlorinated aromatic hydrocarbons such as, for example, monochlorobenzene, dichlorobenzenes, trichlorobenzenes, the corresponding toluenes and xylenes and chloroethylbenzene, have proved to be suitable inert solvents. Monochlorobenzene, dichlorobenzene or mixtures of these chlorobenzenes are preferably used as inert organic solvents. The amount of solvent is expediently chosen such that the reaction mixture has an isocyanate content of 2 to 40 wt. %, preferably between 5 and 20 wt. %, based on the total weight of the reaction mixture. When the phosgenation has ended, the excess phosgene, the inert organic solvent and/or mixtures thereof, are separated off from the reaction mixture by distillation.

The products, which are known from the prior art, of the polymeric MDI series containing di- and polyisocyanates of the diphenylmethane series which are dinuclear and more than dinuclear, and of the monomeric MDI series containing dinuclear diisocyanates of the diphenylmethane series, can be prepared from the crude MDI obtained. In particular, high-viscosity polymeric MDI types of 80 to 3,000 mPas at 25° C., technical-grade 4,4'-MDI and/or technical-grade 2,4'-MDI as well as mixed forms thereof can be prepared. These products can be separated off from the crude MDI in accordance with the prior art, for example, by distillation. These products are suitable for use as raw materials for polyurethane preparation in the form of polymers and prepolymers by reaction with polyols.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

General Instructions for the Experiments:

389 p of a 32.1 wt. % strength aqueous formaldehyde solution were added dropwise to 931 g aniline at 80° C. over the course of 20 mm, while stirring. After the addition was completed, the mixture was stirred for a further 5 min and a phase separation was carried out at 70 to 80° C. Then, 114 g of a 32.0 wt. % strength aqueous hydrochloric acid was added to the organic phase, the aminal, at 45° C. over the course of 20 min, while stirring. (See Table 1 for content of metal ions which are divalent and more than divalent present in the hydrochloric acid.) After the reaction mixture was stirred at 45° C. for 30 mm, it was heated up to 60° C. and stirred at 60° C. for a further 30 min. The reaction temperature was then increased to 104° C. The reaction mixture was stirred at this temperature for a further 10 hours in order to bring the reaction to completion.

62.3 g of a 33 wt. % strength sodium hydroxide solution were added to 500 g of the acidic reaction mixture prepared in this way in a stirred vessel at a temperature of 90° C., while stirring. The two-phase mixture formed was subsequently stirred at 90° C. for approx. 5 min. For phase separation at 90° C., the stirrer was switched off. The contents of the individual and the sum of all the metal ions which are divalent and more than divalent in the hydrochloric acid employed, and the results of the examples according to the invention, and of the comparison examples can be seen from the following table.

TABLE 1

| | Content of metal ions which are divalent and more than divalent in the hydrochloric acid | | | | | |
| --- | --- | --- | --- | --- | --- | --- |
| | Al [wt. %] | Ca [wt. %] | Fe [wt. %] | Mg [wt. %] | Total [wt. %] | Rag |
| Comparison Example 1 | 0.0010 | 0.0011 | 0.0020 | 0.0004 | >0.001 | yes |
| Comparison Example 2 | 0.0005 | 0.00055 | 0.0010 | 0.0002 | >0.001 | yes |
| Comparison Example 3 | 0.0002 | 0.0003 | 0.0005 | 0.0001 | >0.001 | yes |
| Example 1 | 0.00013 | 0.00014 | 0.00025 | 0.00005 | <0.001 | no |
| Example 2 | <0.00002 | <0.00002 | <0.00002 | <0.00002 | <0.001 | no |

Comparison Examples 1 to 3 illustrate the undesirable formation of the rag or the development of a rag layer at the interface between the organic and the aqueous phase. No rag or no rag layer is formed in Examples 1 and 2 which are according to the present invention.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of di- and polyamines of the diphenylmethane series comprising reacting aniline with formaldehyde in the presence of hydrochloric acid contains the metal ions $Ca^{2+}$, $Mg^{2+}$, $Al^{3+}$ and/or $Fe^{2+}$, wherein the hydrochloric acid employed contains a total of less than 0.001 wt. % of metal ions which are divalent and/or more than divalent, with each of the metal ions $Ca^{2+}$, $Mg^{2+}$, $Al^{3+}$ and/or $Fe^{2+}$ being resent in concentrations of less than 0.0003 wt. %.

2. The process of claim 1, wherein the hydrochloric acid employed contains a total of less than 0.0005 wt. % of other metal ions which are divalent and/or more than divalent.

3. The process of claim 1, wherein the hydrochloric acid employed contains a total of less than 0.0003 wt. % of other metal ions which are divalent and/or more than divalent.

4. The process of claim 1, wherein the reaction of aniline with formaldehyde in the presence of hydrochloric acid is carried out with a degree of protonation of less than 15%.

5. A process for the preparation of di- and polyisocyanates of the diphenylmethane series, comprising reacting the di- and polyamines of the diphenylmethane series produced by the process of claim 1, with phosgene, to yield di- and polyisocyanates of the diphenylmethane series.

* * * * *